United States Patent
Sinha et al.

(10) Patent No.: US 9,919,922 B2
(45) Date of Patent: Mar. 20, 2018

(54) BIONANOSENSOR DETECTION DEVICE

(76) Inventors: Saion Kumar Sinha, Fairfield, CT (US); Eva Terezia Sapi, Madison, CT (US)

(*) Notice: Subject to any disclaimer, the term of this patent is extended or adjusted under 35 U.S.C. 154(b) by 504 days.

(21) Appl. No.: 13/063,623

(22) PCT Filed: Oct. 1, 2009

(86) PCT No.: PCT/US2009/059208
§ 371 (c)(1),
(2), (4) Date: Jun. 1, 2011

(87) PCT Pub. No.: WO2010/039941
PCT Pub. Date: Apr. 8, 2010

(65) Prior Publication Data
US 2012/0178639 A1    Jul. 12, 2012

Related U.S. Application Data

(60) Provisional application No. 61/194,986, filed on Oct. 2, 2008.

(51) Int. Cl.
C12Q 1/68 (2006.01)
B82Y 30/00 (2011.01)
B82Y 15/00 (2011.01)

(52) U.S. Cl.
CPC ............. B82Y 30/00 (2013.01); B82Y 15/00 (2013.01); C12Q 1/689 (2013.01); C12Q 1/6825 (2013.01)

(58) Field of Classification Search
CPC ....... B28Y 15/00; C12Q 1/689; C12Q 1/6825
See application file for complete search history.

(56) References Cited

U.S. PATENT DOCUMENTS 6,376,177 B1    4/2002  Poponin
6,824,974 B2   11/2004  Pisharody et al.
(Continued)

FOREIGN PATENT DOCUMENTS

JP    2008/222765 A      9/2008
WO    WO 2004/020450 A1  3/2004
(Continued)

OTHER PUBLICATIONS

Robert R. Johnson et al., "Probing the Structure of DNA-Carbon Nanotube Hybrids with Molecular Dynamics," Nano Lett. 8,1(2008), p. 69, American Chemical Society, US.
(Continued)

Primary Examiner — Jonathan M Hurst
(74) Attorney, Agent, or Firm — Cantor Colburn LLP

(57) ABSTRACT

The present invention is directed to a nucleic acid detection device and method that incorporates bio-nanosensor technology to detect duplex DNA. The device is particularly applicable in detecting the presence or absence of duplex DNA and its correlation to the diagnosis of infectious diseases. In one embodiment, the infectious disease is Lyme disease or a bacterial or viral infection. The device comprises a bio-nanosensor element comprising ssDNA primed nanotubes, either single walled or multi-walled. The method comprises contacting the bio-nanosensor element with a test solution potentially containing DNA of interest. DNA of interest that hybridizes to the ssDNA results in a measurable change in the electrical properties of the bio-nanosensor. Correlations between the results provided by the device and the presence of disease states can result in rapid diagnosis of diseases such as Lyme disease or foodborne infections such as salmonellosis.

14 Claims, 5 Drawing Sheets

(56) References Cited

U.S. PATENT DOCUMENTS

| | | |
|---|---|---|
| 6,958,216 B2 | 10/2005 | Kelley et al. |
| 7,052,854 B2 | 5/2006 | Melker et al. |
| 7,318,908 B1 | 1/2008 | Dai |
| 2001/0053535 A1 | 12/2001 | Bashir et al. |
| 2002/0172963 A1* | 11/2002 | Kelley et al. ............ 435/6 |
| 2003/0134410 A1* | 7/2003 | Silva ............ B01L 3/5027 |
| | | 435/287.2 |
| 2004/0106203 A1* | 6/2004 | Stasiak et al. ............ 436/49 |
| 2007/0045756 A1 | 3/2007 | Chang et al. |
| 2007/0134696 A1 | 6/2007 | Zheng et al. |
| 2007/0158766 A1 | 7/2007 | Lieber et al. |
| 2007/0172829 A1 | 7/2007 | Exner |
| 2007/0212677 A1 | 9/2007 | MacDonald et al. |
| 2007/0278111 A1 | 12/2007 | Boussaad et al. |
| 2008/0004368 A1 | 1/2008 | Wang et al. |
| 2008/0009002 A1* | 1/2008 | Gruner ............ B82Y 15/00 |
| | | 435/6.11 |
| 2008/0044651 A1 | 2/2008 | Douglas |
| 2008/0131880 A1 | 6/2008 | Bortolin et al. |
| 2009/0121727 A1* | 5/2009 | Lynch et al. ............ 324/609 |

FOREIGN PATENT DOCUMENTS

| | | |
|---|---|---|
| WO | 2006024023 A2 | 3/2006 |
| WO | WO 2006/071895 A2 | 7/2006 |
| WO | WO2008012728 A1 | 1/2008 |
| WO | 2008018834 A1 | 2/2008 |
| WO | WO 2008/027078 A2 | 3/2008 |
| WO | WO 2008/051316 A2 | 5/2008 |

OTHER PUBLICATIONS

Baker, Sarah et al., "Covalently bonded adducts of DNA with single-walled carbon nanotubes: Synthesis and hybridization," Nano Letters 2, 1413-1417, Oct. 15, 2002, ACS.

Keren, Kinneret et al., "DNA-templated carbon nanotube field-effect transistor," Science 302, 1380-1382, Nov. 21, 2003, AAAS.

Supplementary European Search Report, Application No. EP 09818504, European Patent Office, Apr. 3, 2012.

Zelada-Guillen, Gustavo A. et al., "Immediate Detection of Living Bacteria at Ultralow Concentrations Using a Carbon Nanotube Based Potentiometric Aptasensor," Angew. Chem. Int. Ed. 48, 7334-7337, 2009, Wiley-VCH Verlag GmbH & Co. KGaA, Weinheim, Germany.

\* cited by examiner

BIONANOSENSOR DETECTION DEVICE

CROSS-REFERENCE TO RELATED APPLICATIONS

This application is the U.S. National Stage of International Application No. PCT/US2009/059208, filed Oct. 1, 2009, which claims the benefit of U.S. Provisional Application No. 61/194,986, filed Oct. 2, 2008, the disclosures of which are incorporated herein by reference in their entirety.

SEQUENCE LISTING

A sequence listing has been filed with this application in an ASCII text file; the material in that ASCII text file is incorporated by reference herein. The ASCII text file is named "103131.txt", has a creation date of Oct. 2, 2008, and a size of 5 Kbytes.

BACKGROUND THE INVENTION

1. Field of the Invention

The invention relates generally to nucleic acid detection devices, and more particularly a detection device, that incorporates bionanosensor technology to detect duplex DNA. The device is particularly applicable in detecting the presence or absence of duplex DNA and its correlation to the diagnosis of infectious diseases including tick-borne infections and coinfections such as Lyme disease, babesiosis, anaplasmosis, bartonellosis, and the like, foodborne disease such as salmonellosis, and diseases relating to viral infections such as flu or H1N1.

2. Description of the Related Art

A biosensor is a device for the detection of the presence of an analyte, such as DNA, proteins, peptides, or small molecules, using known interactions between a targeted analyte and a binding agent, typically a macromolecule. Biosensors have been used, for example, in blood glucose monitoring for diabetics, remote sensing of airborne bacteria, identification of health related targets, genetic screening and the like. Biosensors also have utility in disease prevention, diagnosis, and management.

An infectious disease is any disease caused by a pathogen which subsequently grows and multiplies in the body. Infectious diseases have been a serious issue for humans for hundreds of years, and can result in enormous human suffering. For example, Lyme disease, or borreliosis, is an emerging infectious disease caused by at least three species of bacteria belonging to the genus *Borrelia*. *Borrelia burgdorferi* is the predominant cause of Lyme disease in the United States, whereas *Borrelia afzelii* and *Borrelia garinii* are implicated in most European cases. Early manifestations of infection of Lyme disease may include fever, headache, fatigue, depression, and a characteristic skin rash called erythema migrans. Left untreated, late manifestations involving the joints, heart, and nervous system can occur. In a majority of cases, symptoms can be eliminated with antibiotics, especially if diagnosis and treatment occur early in the course of illness. Late, delayed, or inadequate treatment can lead to late manifestations of Lyme disease which can be disabling and difficult to treat. *Salmonella enterica* is a bacterium which causes salmonellosis, a common foodborne infection/intoxication in humans. Rapid and sensitive detection methods of *Salmonella* in a food supply would inhibit and even prevent major outbreaks of salmonellosis. Furthermore, early detection of *Salmonella* pathogenic DNA in a patient's blood would lead to prompt early treatment. These are but two examples of how early treatment of infectious diseases is often critical to effective treatment. It is therefore paramount that infectious diseases be identified early and quickly.

Identification of specific infectious diseases is currently performed in a variety of ways known in the art, including chemical and physical assays, and microscopic examinations. Although various methods and devices are available for detecting an infectious disease, it is appreciated that there is still a need for a reliable, sensitive, simple, convenient, versatile, and cost-effective method to detect the presence of a disease-causing pathogen in body fluids, food samples, water samples, air samples at the earliest stage possible to prevent the spread of the disease and prevent more serious health harms. There is also a need for a detection device that can be used in clinical or field setting and requires only minimal training to use.

Since their discovery, nanotubes have found extensive use in the fields such as electronics, optics, and other fields of materials science. It has been suggested that nanotubes can be used to detect biomolecules of interest, such as proteins and nucleic acids. For example, U.S. Pat. No. 6,376,177 discloses a gene probe biosensor employing field surface enhanced Raman scattering for direct spectroscopic detection of hybridized molecules without the need for labels.

U.S. Pat. No. 7,052,854 discloses a nanostructure-based assembly that is applied to bodily fluid samples for the ex vivo detection of analytes/biomarkers of interest.

U.S. Pat. No. 6,958,216 discloses a biological sensing device including a pair of carbon nanotube tubules at a fixed distance apart, and a biological molecule attached to the carbon nanotube tubules through a metallic material. The biological molecules provide electrical connectivity between the pair of nanotubes tubules.

U.S. Pat. No. 6,824,974 discloses a biosensor includes a first electrode, a second electrode and a binding agent such as a biological macromolecule connecting the first electrode and the second electrode.

Zelada-Guillen et al. (Angew. Chem. Int. Ed. (2009) 48:7334-7337) disclose a method and device for detecting living bacteria using a carbon nanotube-based potentiometri aptasensor. In this invention, *Salmonella* bacteria are attached directly to functionalized SWCNT which causes the pH of the medium to change. The change in pH is correlated with the concentration of bacteria in the medium.

What is needed in the art is a convenient, cost effective, and rapid biosensor detection device that is effective to detect the presence of DNA of interest, and in particular DNA of an infectious organism. The present invention is believed to be an answer to these needs.

BRIEF SUMMARY OF THE INVENTION

In one aspect, the present invention provides a bio-nanosensor detection device for detection of the presence of a disease causing bacteria. The device comprises a bio-nanosensor element, where the bio-nanosensor element comprises a plurality of single stranded nucleic acid primed carbon nanotubes. The bio-nanosensor detection device may also include a heating element with accurate temperature monitoring supporting the nanosensor element, a LED indicator, a constant current source where both the LED indicator and the current source are coupled to the bio-nanosensor element. A meter to measure changes in electrical properties may optionally be coupled to the bio-nanosensor element. In a preferred embodiment, the single stranded nucleic acid is a pathogen DNA such as *Borrelia burgdorferi* or *Salmonella enterica* specific DNAs.

The detection device is portable, easy to use and inexpensive. It can be used in a physician's office or at the point of care or at the point of need (e.g., in the field, in food processing facilities) to provide rapid results.

In another aspect, the present invention provides a method for detecting infectious diseases. The method includes providing a bio-nanosensor detection device, providing a sample suspected of containing an infectious disease causing bacteria, heating the bio-nanosensor element for a sufficient time to denature the DNA of the bacteria and to facilitate the hybridization of the denatured DNA with a single stranded pathogen specific DNA, and measuring the change in one or more electrical properties (e.g., conductance or electrical current flow) of the bio-nanosensor with respect to the baseline electrical properties whereby the presence of the infectious disease causing bacteria is detected. In one embodiment, the pathogen specific DNA is either *Borrelia burgdorferi* or *Salmonella enterica* specific DNA.

BRIEF DESCRIPTION OF THE FIGURES

The written description of the invention will be better understood when taken in conjunction with the following Figures in which.

DETAILED DESCRIPTION OF THE INVENTION

Figure 1:
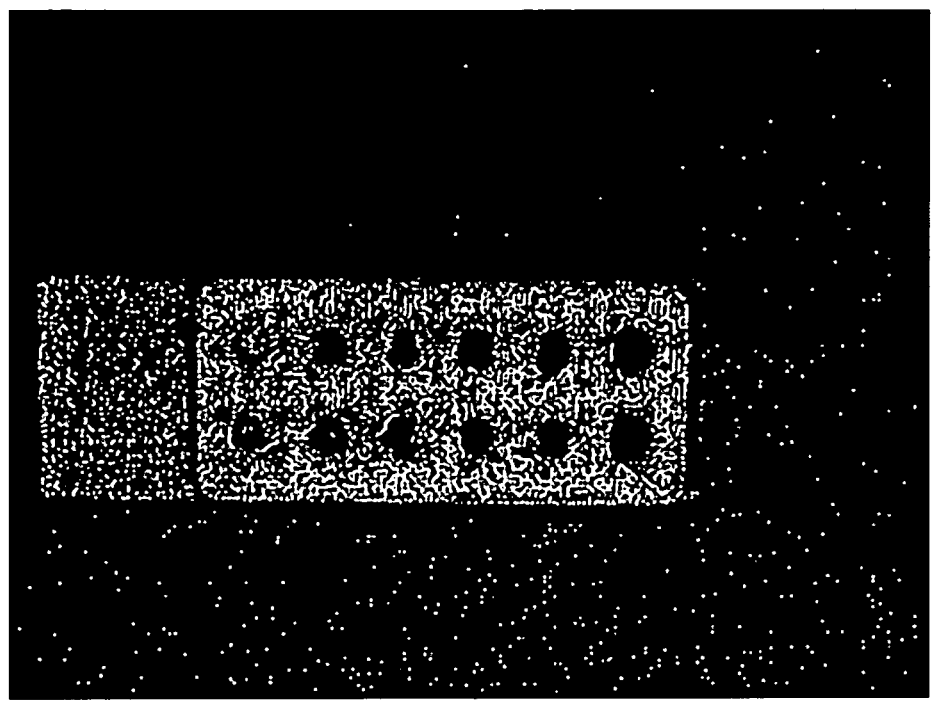
FIG. 1 is a photograph showing a bio-nanosensor array according to one embodiment of the invention.

The inventors have developed a bio-nanosensor detection device that can detect, among other things, the presence of disease causing bacteria. The present device uses carbon nanotubes primed with single stranded nucleic acids having a specified sequence as a bio-nanosensor element. The bio-nanosensor device of the present invention detects hybridization between the known single stranded nucleic acid on the carbon nanotubes and a complementary nucleic acid strand in a sample through measurable changes in electrical properties, including, but not limited to, resistance, conductivity, current flow, and the like. In one embodiment, DNA specific to a disease causing bacteria can be detected, thus allowing the diagnosis of the disease. In another embodiment, DNA from pathogen (infectious disease-causing bacteria) may be detected.

The device of the present invention has very broad applications in the detection of pathogens. Any pathogen that contains nucleic acids is suitable for detection using the device of the present invention. For example, the device of the present invention is effective to detect the presence of various infectious disease-causing bacteria such as *Borrelia burgdorferi*, the bacteria that is responsible for Lyme disease or *Salmonella enterica* the causative agents of salmonellosis. Additional pathogens include, for example, Babesia, Bartonella, Anaplasma, Mycoplasma, viruses such as West Nile virus and Influenza (common flu virus), and encompass a variety of diseases such as Lyme disease, salmonellosis, malaria, encephalitis, meningitis, West Nile fever, and the like. The device is particularly applicable in detecting the presence or absence of duplex DNA and its correlation to the diagnosis of infectious diseases including tick-borne infections and coinfections such as Lyme disease, babesiosis, anaplasmosis, bartonellosis, and the like, foodborne disease such as salmonellosis, and diseases relating to viral infections such as flu or H1N1. The device and method of the present invention have particular applicability in the areas of human disease, animal and livestock disease, foodborne disease, food production, environmental and ecological studies, and combating bioterrorism. Other applications will be readily apparent to those of skill in the art.

The device of the present invention may be used to detect pathogens carried by many vectors such as ticks, mosquitoes, flies, spiders, fleas, or any other disease-carrying insect. The device of the invention also has the capability to detect circulating DNA in saliva or any other sample. Moreover, the source of any sample analyzed in the device of the present invention may be from any source, including foods, air, water, body fluids, and the like.

The device of the invention is portable, easy to operate, inexpensive, and biodegradable, and has the advantage of being suitable for both clinical and field testing. The rapid results provided by the device is advantageous in the prevention, diagnosis, and treatment of infectious diseases because infectious disease patients can now be detected at a very early stage, thus preventing the spread of the disease and causing more serious health issues.

The device of the present invention is also advantageous because its operation is not dependent on nucleic acids of a certain length or potential, and as a result, the complicated task of a fixed position of DNA attachment is not required. It is also very sensitive, having the capability of detecting nucleic acid concentrations lower than 1 picoMolar ($10^{-12}$ M). Hence it can be used in physicians' offices and at the point of care and provide rapid results concerning diagnosis and treatment.

Carbon nanotubes are allotropes of carbon with a nanostructure that has an extremely high length-to-diameter ratio. Typically, nanotubes are categorized as single walled carbon nanotubes (SWCNT) and multi-walled carbon nanotubes (MWCNT). The structure of a SWCNT can be envisioned as a seamless cylinder formed by wrapping a one-atom-thick layer of graphite. A MWCNT is analogous to an electrically conductive molecular wire. It is like an ordinary conducting wire but very small in size. Most MWCNTs are a thousand times smaller than a strand of human hair. A bio-nanosensor, which contains numerous MWCNTs, can be thought of as a sensor comprising nets of wires, where some of the wires are in percolating contact near the surface of the sensor. Hence, the sensor's electrical resistance is dependent on the surface conditions. A bio-nanosensor that contains SWCNTs exhibits similar properties.

Figure 2A:
FIG. 2(a) is an atomic force microscope (AFM) magnified image of the sensor surface without any DNA.
Figure 2B:
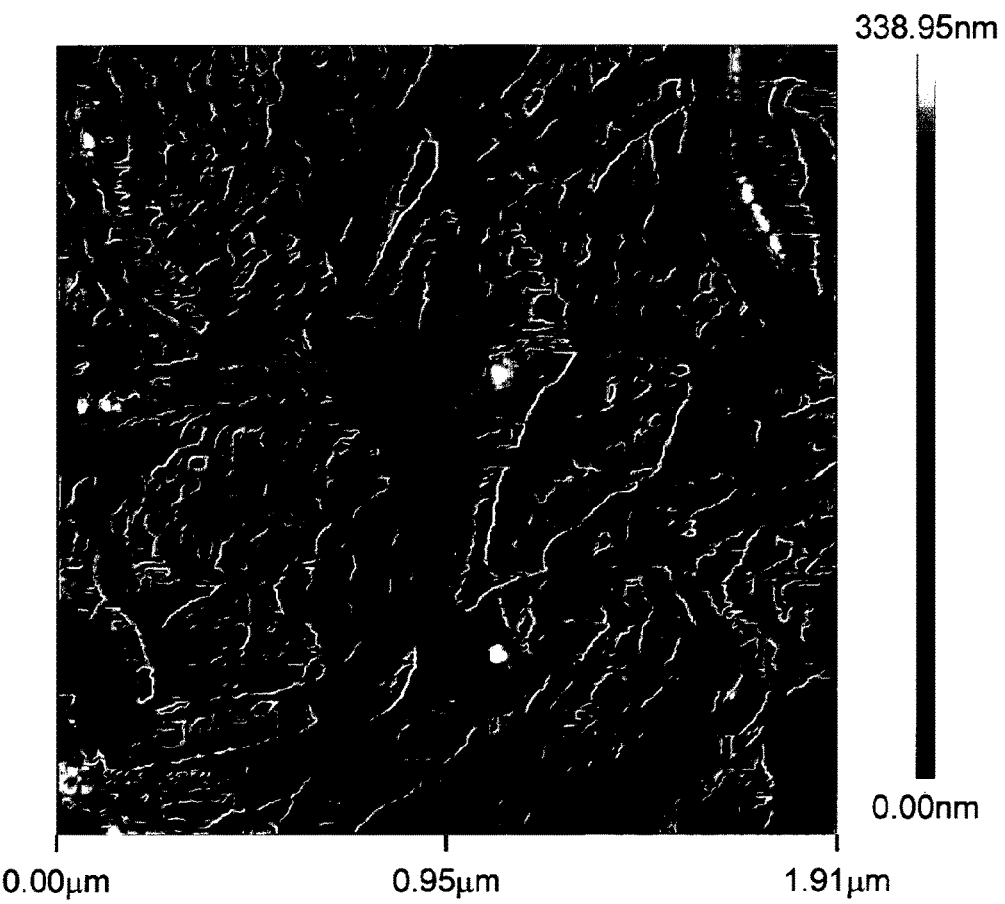
FIG. 2(b) is an atomic force microscope magnified image of a single stranded DNA wrapping around a matrix of multi-walled carbon nanotubes on the sensor surface after adding only one type of primer.

When a single stranded DNA (ssDNA) coats the surface of the sensor by wrapping around a MWCNT (as shown in FIG. 2b), it can impede the electron flow of an electrical current. When a complementary DNA (cDNA) strand hybridizes to this ssDNA, it can further impede the electron flow. In both cases, the electrical properties, for example the resistance, of the sensor will be changed in a way that can be easily measured before and after the DNA hybridization process. Therefore, by measuring the change of these electrical properties the presence or absence of hybridized duplex DNA can be detected. Since the resistance depends critically on the MWCNT network, the bio-nanosensor is very sensitive to the amount of DNA hybridized. It can also be used to measure the proportion of the DNA that is hybridized.

It will be appreciated by the skilled artisan that the carbon nanotubes of the present invention may be coated with one or more types of ss-DNA. In one embodiment, the device of the present invention includes carbon nanotubes that are coated with more than one type of ss-DNA so that multiple pathogens may be detected simultaneously. In a particular embodiment and through the proper selection of ss-DNAs, it is possible to simultaneously detect tick-borne infections, water contaminants, food pathogens, etc.

Examples

A number of prototypes of bio-nanosensors were fabricated, with MWCNTs and SWCNTs from various commercial sources (e.g., Helix Medical, Bayer Materials, BuckyUSA, Carbon Solutions). The MWCNTs used in the present invention had a diameter of about 5-40 nm, a length of about 0.5-2 microns and a purity of 95%. Some of the SWCNT (diameter ~0.5-5 nm, and length ~0.5-2 micrometer) were synthesized by a chemical vapor deposition system with an alcohol precursor at the University of New Haven (West Haven, Conn.). In general, carbon nanotube dimensions in this invention range from about 0.5 nm (single wall carbon nanotubes) to about 40 nm (double wall carbon nanotubes). The carbon nanotubes of the invention may be made from carbon or other 1-D nanomaterials such as silicon nanowire.

A suspension of both types of carbon nanotubes were made in deionized (DI) water by sonicating a mixture of the carbon nanotubes with 1% of sodium dodecylsulfate (SDS). The presynthesized forward ss-DNA or reverse ss-DNA were admixed with this carbon nanotube suspension at room temperature and atmospheric pressure. The ss-DNA can be a DNA of any disease-causing bacteria. In a preferred embodiment, the DNA is a single stranded *Borrelia burgdorferi* or *Salmonella enterica* specific oligonucleotide. After the suspension containing CNTs, SDS and ss-DNA is prepared, it was spray coated on a substrate using a spray painting gun along with a binding agent simultaneously heating the substrate to an elevated temperature. In another embodiment the CNTs were painted on top of the substrate, which already had a layer of starch which was acting as a binder. In another embodiment, the forward ss-DNA and the reverse ss-DNA were applied to the sensor in a buffer solution. After completely drying the substrate in a nitrogen atmosphere, electrical contacts were made with silver paint. The sample was annealed several times to get consistent contacts. Standard 4-Probe measuring technique was used to measure the conductance of the bio-nanosensor. Typical measurements were made after 3 annealing cycles of the sample. A typical annealing cycle is to ramp-up the temperature at 5° C./min to the melting point of the DNA and then keeping it at that temperature for 1-5 mins.

The substrate can be glass, plastic, or any other material that the CNTs-DNA mixture can adhere to. In one embodiment, the preferred substrate was printed circuit board (PCB) with prefabricated copper contacts or plexiglass with prefabricated contacts. The appropriate temperature of the substrate during the coating process can be determined based on the binder and the substrate material used and is within the skill of one of ordinary skill in the art. In one embodiment, a glass substrate is heated to about 45-50° C. during the coating process. The binder chosen in this project was organic that does not denature DNA. Examples of useful binders include starch, albumin, agarose and some nonconducting proteins.

A bio-nanosensor array can comprise multiple bio-nanosensors. A sensor array according to one embodiment of the invention is shown in FIG. 1. Each of the black circles is a nano-biosensor and they are connected in an array with silver paint. The wires observed are the pre-fabricated copper-wires on the PCB that is connected to the measurement device. An atomic force microscope (AFM) magnified image of a bio-nanosensor is shown in FIG. 2a. The image illustrates a dense matrix of MWCNTs. The MWCNTs are about 30 nm in diameter. This image is taken before the application of any DNA to the sensor. FIG. 2b shows the atomic force microscopy image of a DNA wrapping around a MWCNT. This is the image on the sensor surface without any hybridization but an evidence that DNA can couple to MWCNT efficiently. As shown in FIG. 2b, the larger cylinders are the MWCNT and the ss-DNA can be seen wrapping around the MWCNT. This wrapping is speculated to cause the change of resistance.

Measurement of electrical properties, such as conductance, of a bionanosensor according to one embodiment of the invention was performed to determine if the sensor was sensitive enough to detect the hybridization of cDNA of two unrelated human pathogens *Borrelia burgdorferi*, Lyme disease causing bacteria and *Salmonella enterica* a common foodborne pathogen. Complementary oligonucleotides specific to *Borrelia* flagellin gene (30 bases long/each) or *Salmonella* invasion gene (invA gene; 23 bases long/each) were used for these experiments. The sequence listing of the *Borrelia* flagellin gene can be found at Accession No. FJ518808 and the sequence listing of the *Salmonella* InvA gene can be found at Accession No. on the NCBI website (http://www.nebi.nlm.nih.gov).

Figure 3:
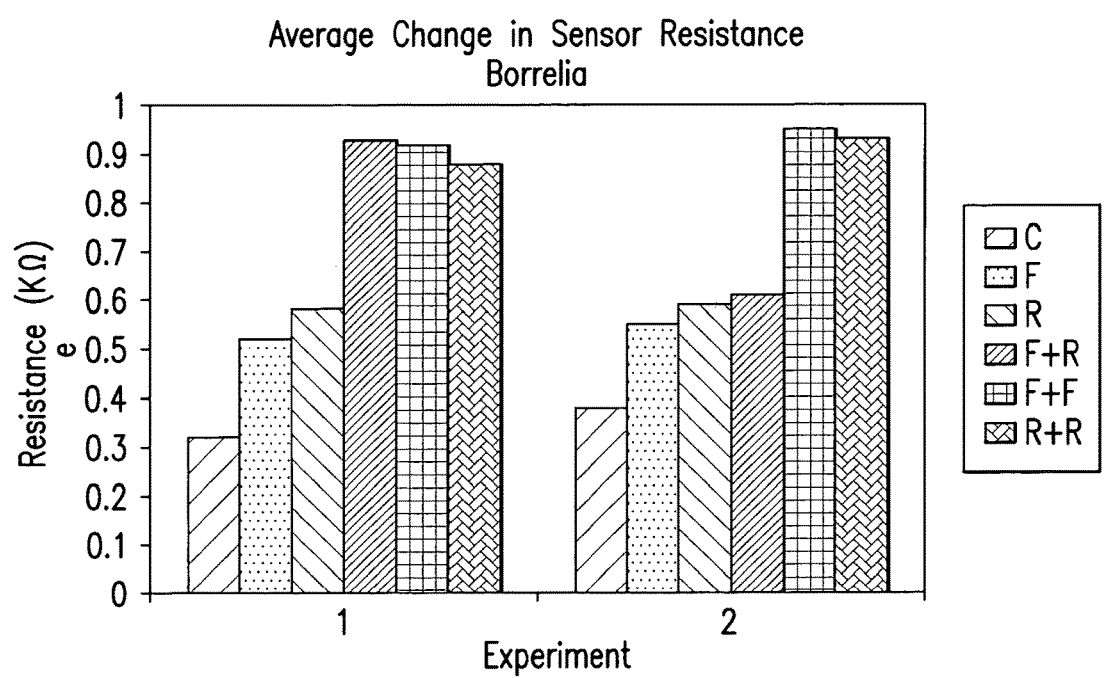
FIG. 3 is a graph showing the change in the bio-nanosensor resistance after the sensor is contacted with *Borrelia burgdorferi* specific testing samples.

Using the embodiment of the invention described above, the following results were obtained. First, the resistance of the sensor according to one embodiment of the invention was measured after adding either the forward (F) *Borrelia* or *Salmonella* oligonucleotides or complementary oligonucleotides (R) either separately or together. The sequence of F and R *Borrelia* specific oligonucleotides are 5'-CATATTCA-GATGCAGACAGAGGTTCTATAC-3' (SEQ ID NO:1) and 5'-GTATAGAACCTCTGTCTGCATCTGAATATG-3' (SEQ ID NO:2) respectively, and the sequence for *Salmonella* specific oligonucleotides are 5'-GCGTTCTGAACCTTTG-GTAATAA-3' (SEQ ID NO:3) and 5'-TTATTAC-CAAAGGTTCAGAACGC-3' (SEQ ID NO:4) respectively. A change of resistance was observed in experiments with both pathogenic primers and found to be comparable; a data which indicates that the sensor can be used to detect different pathogenic DNA regardless of the sequence. The summary of the results is shown in FIG. 3 (*Borrelia*) and FIG. 4. (*Salmonella*).

Figure 4:
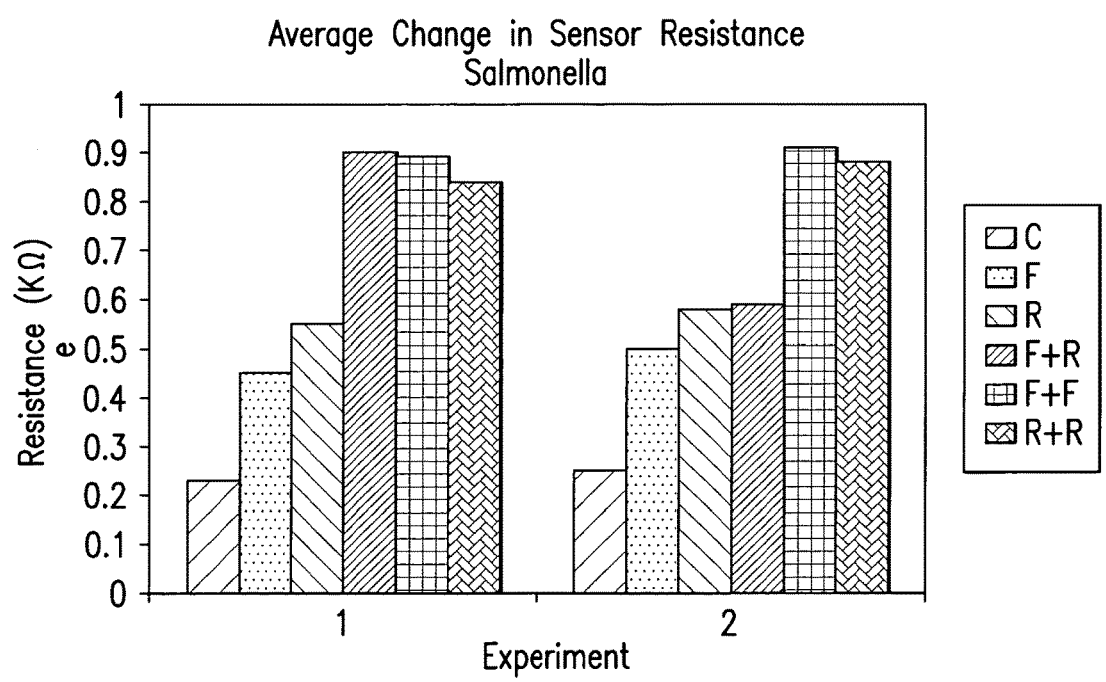
FIG. 4 is a graph showing the change in the bio-nanosensor resistance after the sensor is contacted with *Salmonella enterica* specific testing samples.

As shown in FIGS. 3 and 4, both *Borrelia* or *Salmonella* specific F and R DNA oligonucleotides were either added simultaneously (Experiment 1) or sequentially (Experiment 2) to the sensors to test whether the observed effect is due to unspecific or complementary hybridization of the primers. The sensor was then heated to 90° C. for 1 minute (denaturing step) and cooled to 48° C. 1 minute (annealing step) in a buffered environment to promote potential DNA hybridization. After this process, the resistance was again measured. An additional experimental condition was also included where F or R primers added twice (simultaneously or sequentially in experiment 1 and 2 respectively) to analyze whether the resistance can change when there is no complementary hybridization but double amount of primer is present.

FIG. 3 shows the average change in sensor resistance after addition of different combinations of *Borrelia burgdorferi* specific oligonucleotides. In Experiment 1, the resistance of the sensor was measured after adding either the forward (F) *Borrelia* specific oligonucleotide or complementary oligonucleotide (R) separately or mixing the different *Borrelia* specific nucleotides before adding it to the sensor simultaneously (F+R or F+F or R+R). In Experiment 2, the sensor was first primed with one of the *Borrelia* specific oligonucleotides (F or R) and first the sensor resistance was measured and after a second primer added sequentially (F+R or F+F or R+R) and the resistance is measured again.

FIG. 4 shows the average change in sensor resistance after addition of different combinations of *Salmonella enterica* specific oligonucleotides. In Experiment 1, the resistance of the sensor was measured after adding either the forward (F) *Salmonella* oligonucleotide or complementary oligonucleotide (R) separately or mixing the different *Salmonella* specific nucleotides before adding it to the sensor (F+R or F+F or R+R). In Experiment 2, the sensor first primed with one of the *Salmonella* specific oligonucleotides (F or R) and first the sensor resistance was measured and after a second primer added sequentially and the resistance is measured again ((F+R or F+F or R+R).

FIGS. 3 and 4 show the absolute number of the resistance of the sensor in the different experimental conditions for *Borrelia* and *Salmonella* oligonucleotides respectively. Adding single stranded *Borrelia* or *Salmonella* primers to the sensor increased the resistance readings by 2-fold (both for F and R primers) in both experiments which indicates that the primers efficiently binding to the CNT and the binding is not sequence dependent. Adding double amounts of identical primer (*Borrelia* F+F or R+R or *Salmonella* F+F or R+R oligonucleotides) further increased the resistance with an additional 2-fold regardless whether the oligonucleotides were mixed before or after to the addition of the sensor; data which suggest that double amount of oligonucleotide will further increase the resistance by binding additional oligonucleotides to the nanoparticles. However, because there is no specific DNA hybridization, it will not replace the complementary oligonucleotides from the CNTs. Furthermore, when complementary oligonucleotide was added sequentially to the sensor which already contained the matching primer; there were a very significant decrease (~40%) observed in the resistance of the sensor which suggest that the hybridization of the complementary oligonucleotides replaced some of the nanoparticle-attached oligonucleotides and significantly lowered the resistance of the sensor.

The sensor's resistance change triggered by the hybridized DNA sample was found to be very specific to complementary oligonucleotides, but not the actual pathogenic sequence therefore the measurement of a sensor's resistance change can serve as a reliable means to detect hybridization for different pathogenic DNA samples. The concentration of the oligonucleotides in these experiments was 0.2 micromolar ($10^{-6}$ M) or 20 picomolar ($10^{-12}$ M) per ml, which is similar to the concentration of the DNA used in PCR based measurements. Hence, the experimental results demonstrate that the presence of a DNA can be detected based on its hybridization and the detection method can be as sensitive as a PCR based method.

Figure 5:
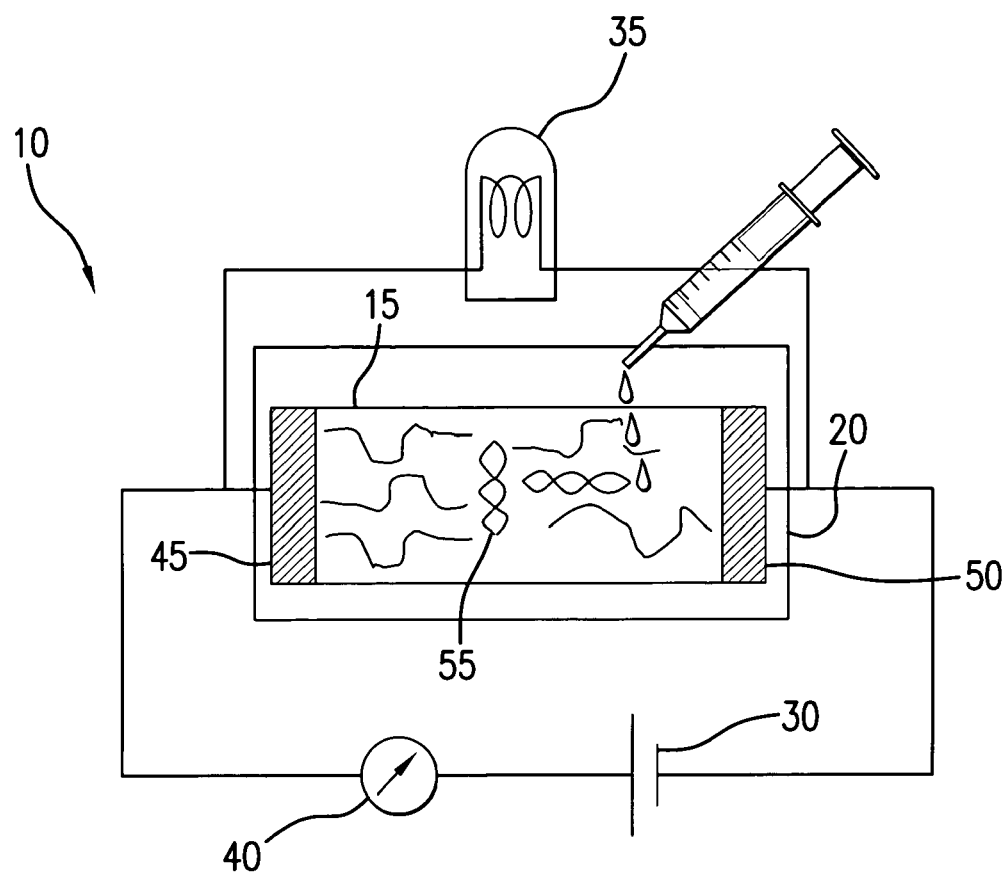
FIG. 5 is a schematic illustration of a bio-nanosensor detection device for detection of a component of interest.

FIG. 5 is a schematic illustration of a bio-nanosensor detection device (10) for detecting a component of interest in accordance with the present invention. The device comprises a bio-nanosensor element (15), a heating tape element (20) with an accurate temperature monitoring component at the back of the bio-nanosensor element, a constant current source (30) and a LED indicator (35), where both the current source and the LED indicator are coupled to the bio-nanosensor element. A monitoring device (40) may also be included to measure and quantify the amount of pathogenic material. As shown in FIG. 5 in one exemplary embodiment, a simple ohm meter is optionally used to measure conductance. It will be appreciated that any type of measuring device may be used, such as a device to measure electrical flow or resistance, or an LED indicator. The AC current source in the device can be used to eliminate stray charging and polarization effects and to increase the sensitivity. The bio-nanosensor element in the detection device comprises a first electrode (45), a second electrode (50) and multiple carbon nanotubes (55) connecting the first and second electrodes, where the carbon nanotubes are primed with a ssDNA of a bacteria specific to a particular disease.

The environed process of operation on clinical samples is as follows: first the clinical sample will be prepared into a 20 microliter droplet of a special lyses buffer, and the resulting fluid suspension will be collected. The heating element, backing the base and supporting the sensing pack, is turned on for an appropriate time, first to denature tick DNA (96-97° C.) and then to facilitate further denature or hybridization step (45-60° C.) with the capture probe. The red LED indicator lights up as soon as there is a match with the pathogenic DNA. The green LED indicator lights up as soon as there is no match with the pathogenic DNA and the sensor works correctly. The yellow light appears if there is a possible fault with the sensor.

The bio-nanosensor detection device according to one embodiment of the invention identifies the presence of pathogenic DNA for a controlled and specifically prepared clinical sample. According to another embodiment, the detection device could be used to detect the bacteria in field samples (tick testing) or food supplies and in clinical samples, for example, urine, saliva, blood and synovial fluid. From these samples, the bio-nanosensor detection device would be able to determine if a person or food supplies are infected or not. Since the sensor identifies particular DNA strands which are unique to pathogenic DNA, it will not signal the presence of any other bacteria or organism and thus it has a high degree of specificity.

Moreover, in addition to identifying the presence of pathogenic material in a sample, the device of the present invention is also capable of quantifying the amount of pathogenic material in a sample based on the degree of change in electrical properties mentioned above. In one exemplary embodiment, the amount of pathogenic material in a sample is proportional to the change in conductivity as compared to a calibrated baseline. It has been found that primers with more base pairs (e.g., longer oligonucleotides) provide a stronger signal and hence better sensitivity as compared to shorter oligonucleotides, and therefore longer oligonucleotides are generally preferred in the method of the invention.

The bio-nanosensor element is biodegradable and inexpensive. The portable sensor will quickly, reliably and sensitively detect the presence of pathogenic DNAs such as Borrelia burgdorferi or Salmonella enterica DNA. A bio-nanosensor array with 15 sensors is expected to have a volume of 10×2×0.5 cm$^3$, with only the top surface being used for sensing. Thus this portable device would be easily and conveniently used by a doctor's office or mobile unit. The device and method of the present invention are also easy to operate and do not require any special skills or training in order to utilize the methods and device.

---

---

What is claimed is:

1. A bio-nanosensor detection device comprising:
a bio-nanosensor element comprising a plurality of carbon nanotubes coated with single stranded pathogen-specific nucleic acids, wherein the carbon nanotubes are precoated with a binding agent prior to operation, each of said plurality of carbon nanotubes having at least a pair of ends electrically coupled to a substrate, the substrate being made from a printed circuit board material; and
an electrical monitoring device comprising a 4-point probe, said 4-point probe comprising
a first electrode positioned on a first end of the substrate and a second electrode positioned on a second end of the substrate, said first electrode and said second electrode in electrical communication with each other through said carbon nanotubes without passing electrical current directly through the single stranded pathogen-specific nucleic acids, said first electrode and second electrode further being in electrical communication with a current source; and
a first voltage terminal and a second voltage terminal, said first voltage terminal and said second voltage terminal in electrical communication with said carbon nanotubes and a signal indicator, said electrical monitoring device having an AC current source that is directly electrically connected to provide an unamplified signal to said signal indicator and said first electrode and said second electrode;
wherein said electrical monitoring device includes an LED indicator that indicates a change in resistance between the electrodes of said bio-nanosensor element without electrical amplification in response to a non-PCR based hybridization between said single stranded pathogen-specific nucleic acid and a complementary nucleic acid in a sample to detect the presence of a pathogen on said bio-nanosensor element.

2. The bio-nanosensor detection device of claim 1, wherein said carbon nanotubes coated with single stranded nucleic acids comprise single stranded nucleic acids having the same sequence.

3. The bio-nanosensor detection device of claim 1, wherein said carbon nanotubes coated with single stranded nucleic acids comprise single stranded nucleic acids having two or more sequences.

4. The bio-nanosensor detection device of claim 1, further comprising a heating element supporting said bio-nanosensor element.

5. The bio-nanosensor detection device of claim 1, further comprising a constant current source coupled to the bio-nanosensor element.

6. The bio-nanosensor detection device of claim 1, wherein the carbon nanotubes coated with single stranded pathogen-specific nucleic acid comprise a single stranded pathogen specific DNA.

7. The bio-nanosensor detection device of claim 6, wherein the single stranded pathogen specific DNA is *Borrelia burgdorferi* or *Salmonella enterica* specific DNA.

8. The bio-nanosensor detection device of claim 1, wherein the bio-nanosensor element is biodegradable.

9. The bio-nanosensor detection device of claim 1, wherein the substrate includes a planar surface, the first end and second end arranged on opposing sides of the planar surface, the plurality of carbon nanotubes being disposed on the planar surface between the first end and the second end.

10. The bio-nanosensor detection device of claim 1, wherein the first electrode and second electrode are fixed to the substrate.

11. The bio-nanosensor detection device of claim 1, wherein the first electrode and second electrode are in electrical communication prior to application of the sample.

12. The bio-nanosensor detection device of claim 1, wherein the complementary nucleic acid in the sample wraps around at least one carbon nanotube of the plurality of carbon nanotubes.

13. The bio-nanosensor detection device of claim 1, wherein the carbon nanotubes are a double wall nanotube having a diameter of 5-40 nm, a length of 0.5-2 microns and a purity of 95%.

14. The bio-nanosensor detection device of claim 1, wherein the carbon nanotubes are a single wall nanotube having a diameter of 0.5-5 nm and a length of 0.5-2 micrometer.

* * * * *

SEQUENCE LISTING

<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Forward Borrelia sequence

<400> SEQUENCE: 1
catattcaga tgcagacaga ggttctatac      30

<210> SEQ ID NO 2
<211> LENGTH: 30
<212> TYPE: DNA
<213> ORGANISM: Artificial Sequence
<220> FEATURE:
<223> OTHER INFORMATION: Reverse Borrelia sequence

<400> SEQUENCE: 2
gtatagaacc tctgtctgca tctgaatatg      30

<210> SEQ ID NO 3
<211> LENGTH: 23
<212> TYPE: DNA
<213> ORGANISM: Artificial Sequence
<220> FEATURE:
<223> OTHER INFORMATION: Forward Salmonella sequence

<400> SEQUENCE: 3
gcgttctgaa cctttggtaa taa      23

<210> SEQ ID NO 4
<211> LENGTH: 23
<212> TYPE: DNA
<213> ORGANISM: Artificial Sequence
<220> FEATURE:
<223> OTHER INFORMATION: Reverse Salmonella sequence

<400> SEQUENCE: 4
ttattaccaa aggttcagaa cgc      23